United States Patent [19]

Butler et al.

[11] Patent Number: 4,855,450

[45] Date of Patent: Aug. 8, 1989

[54] PROCESS FOR THE PREPARATION OF AROMATIC ETHER BISMALEIMIDES

[75] Inventors: John M. Butler, Centerville; Richard P. Chartoff, Cincinnati; James A. Harvey, Kettering, all of Ohio

[73] Assignee: University of Dayton, Dayton, Ohio

[21] Appl. No.: 136,900

[22] Filed: Dec. 22, 1987

[51] Int. Cl.$^4$ .......................................... C07D 403/10
[52] U.S. Cl. ............................ 548/522; 156/902; 428/295; 526/262; 562/412
[58] Field of Search ........................................ 548/522

[56] References Cited

U.S. PATENT DOCUMENTS

| | | | |
|---|---|---|---|
| 3,839,287 | 10/1974 | Kwiatkowski | 528/172 |
| 3,960,887 | 6/1976 | Renard | 528/422 |
| 4,288,583 | 9/1981 | Zahir | 526/262 |
| 4,460,783 | 7/1984 | Nishikawa | 548/549 |
| 4,464,520 | 8/1984 | Adams | 526/262 |
| 4,691,025 | 9/1987 | Domeier | 548/521 |

OTHER PUBLICATIONS

JP-59-168,017 (Abstract), Chem. Abstracts, vol. 102, 46756(d) of 1985.

Butler et al., Conf. of the Soc. of Plastics Eng., vol. 32 (1986) pp. 1311-1315.

Primary Examiner—Donald G. Daus
Assistant Examiner—F. Tsung
Attorney, Agent, or Firm—Biebel, French & Nauman

[57] ABSTRACT

The present invention provides a process for producing aromatic ether bismaleimides of the Formula (II)

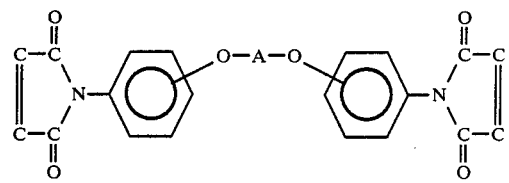

wherein A is a divalent mononuclear or polynuclear aromatic linking group. The process provides good yields and can be scaled up readily to commercial size runs.

The present invention also provides compositions containing at least about 80 weight % of the bismaleimide of Formula (II) above.

20 Claims, 6 Drawing Sheets

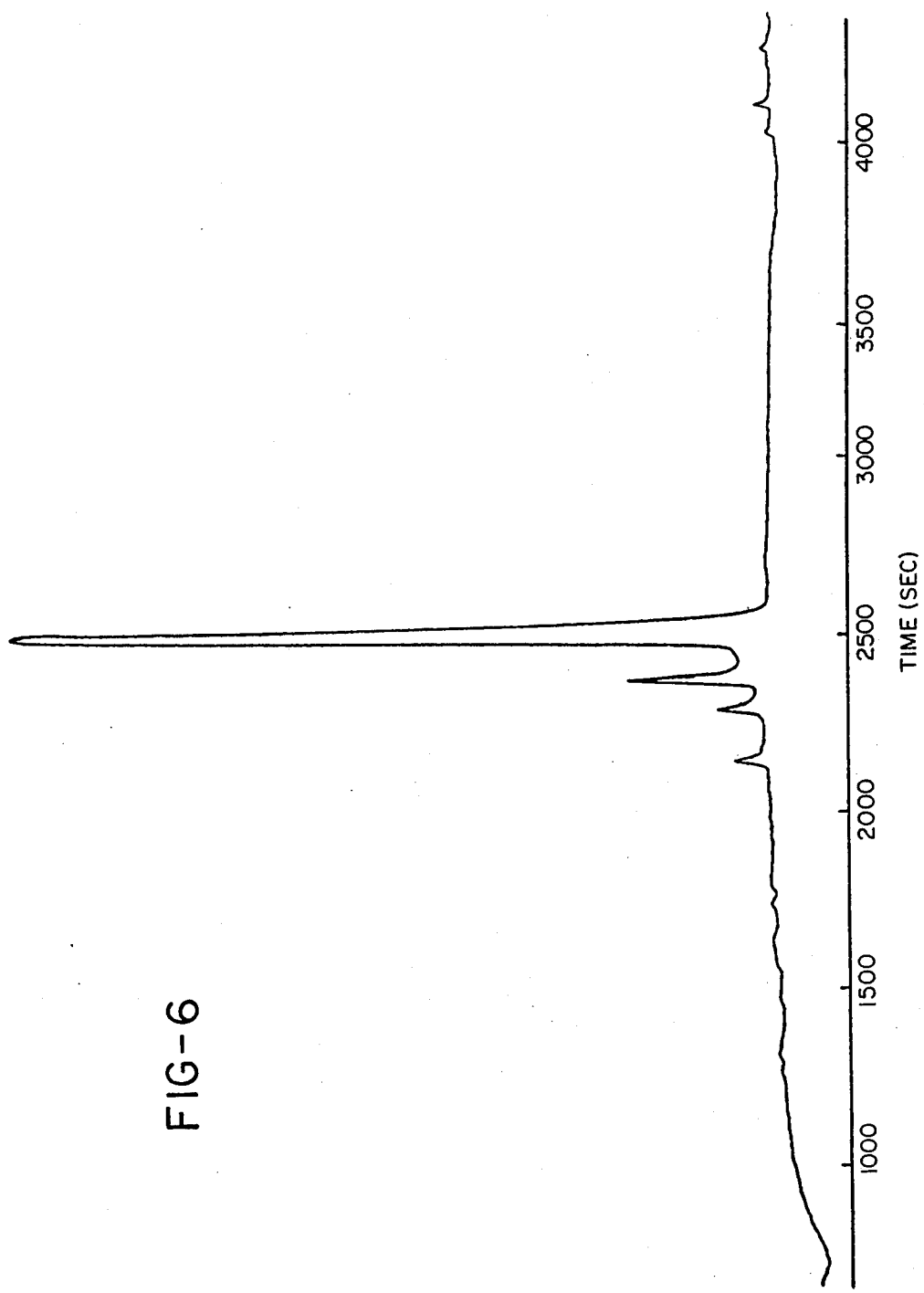

PROCESS FOR THE PREPARATION OF AROMATIC ETHER BISMALEIMIDES

REFERENCE TO COPENDING APPLICATION

This application is a continuation-in-part of our pending application Ser. No. 852,474, filed Apr. 15, 1986, now abandoned. The descriptions of the parent application are incorporated herein by reference.

BACKGROUND OF THE INVENTION

The present invention relates to a process for preparing bismaleimides, and more particularly, to a process for preparing aromatic ether bismaleimides. The invention also relates to an improved and more efficient process for preparing bismaleamic acids which are the precursors of the desired bismaleimides.

Currently, bismaleimide resins are made favorably considered as replacements for epoxy resins because of their greater thermal stability and lower moisture sensitivity. Current epoxy resins have a maximum useful temperature of 350° C. and are weakened by absorbed moisture, particularly when used as matrix resins in fiber reinforced composites. However, the currently available commercial bismaleimides are brittle and are not competitive with epoxies in terms of toughness.

Aromatic ether bismaleimides promise to have greater toughness and lower moisture retention than other bismaleimides because of the ether groups in the main chain and the relatively large monomer chain length. Preliminary data indicate that this type of structure is tougher than state of the art bismaleimides and moisture retention levels are around 2% compared with 4–5% for conventional commercial bismaleimides.

As a result of the aformentioned properties, a great commerical interest in aromatic ether bismaleimides exists at this time. Aromatic ether bismaleimides find application as composite matrix resins for structural composites and electric circuit boards, and as adhesives for bonding structural materials. The aromatic ether bismaleimides may be used alone or in conjunction with other co-monomers.

U.S. Pat. No. 3,839,287 discloses typical polyarylimides which are prepared from aromatic diamines and maleic anhydride. The diamines are reacted with maleic anhydride and then the product is chemically converted to the imidized form by addition of acetic anhydride and triethylamine, or sodium acetate. These polyarylimides are taught to be useful in the preparation of glass cloth prepregs, molding materials, and adhesives.

U.S. Pat. No. 4,288,583 discloses a curable mixture which contains maleimides and phenols. The maleimides may be aliphatic or aromatic, and are prepared by reacting the appropriate amines or polyamines with the maleic anhydride in a polar solvent and in the presence of a catalyst.

U.S. Pat. No. 4,464,520 discloses aromatic bismaleimides which are prepared by using the usual imidization reaction where the imidization is carried out in an inert aprotic solvent using a slight excess of maleic anhydride. Useful inert aprotic solvents include dimethylformamide, dimethylsulfoxide, and dimethylacetamide. Typical reaction temperatures are 40°-60° C. with a preferred range of 50°-60° C. Typical reaction times are 1-1.5 hours. The resulting polybismaleimides are useful as binders in composite molded components, and for circuit board manufacture.

U.S. Pat. No. 4,460,783 is similar to U.S. Pat. No. 3,839,287 in disclosing first reacting aromatic ether diamines with maleic anhydride to form bismaleamic acids which then are reacted with acetic anhydride in the presence of a catalyst such as potassium acetate to convert the amic acid groups to imide groups.

Among aromatic ether bismaleimides, particular commercial interest exists in a bismaleimide of the Formula (I)

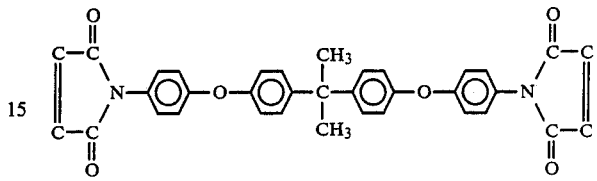

which is derived from Bisphenol A. This bismaleimide is disclosed in U.S. Pat. No. 4,460,783 to Niahikawa et al and U.S. Pat. No. 3,839,287 to Kwiatkowski et al. This compound reportedly can be prepared by reacting Bisphenol A with 4-chloro-1-nitrobenzene to yield the compound 2,2-bis[4(4-nitrophenoxy)phenyl]propane which is reduced to the corresponding diamine 2,2-bis[4-(4-aminophenoxy)phenyl]propane and reacted with maleic anhydride to produce the bismaleimide. The latter reaction proceeds in two stages, first, with formation of the maleamic acid derivative, and then with imidization. For the reasons discussed infra, it is believed that neither the Niahikawa nor the Kwiatkowski process produces the bismaleimide of Formula (I) in significant yield and free of larger concentrations of coproducts.

Several problems are encountered when the Niahikawa reaction sequence is used on an industrial scale. On an industrial scale, the aromatic diamine reactant is employed at a high concentration in the reaction solvent. As the conversion of the aromatic diamine to the maleamic acid increases, the maleamic acid precipitates from the reaction mixture and the reaction mixture becomes too thick to stir even at low concentrations. The mixture has the appearance of an aerosol foam. On a large scale, the temperature cannot be controlled and the mixture does not react uniformly. As a result, a product is obtained which contains high concentrations of by-products. This product is disadvantageous because these by-products interfere with the normal overall curing mechanism of the bismaleimide, and in addition, generate excessive volatiles during cure which results in voids in the cured products.

SUMMARY OF THE INVENTION

An object of the present invention is to provide a process for producing in high yields aromatic ether bismaleimides of the Formula (II)

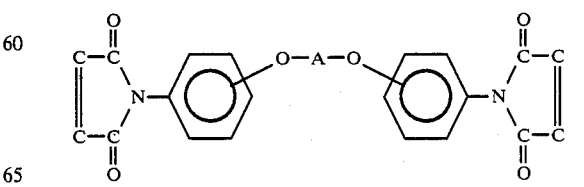

wherein A is a divalent mononuclear or polynuclear aromatic linking group which proceeds with good yields, can be scaled up readily, and provides fewer by-products.

In a preferred embodiment, A in Formula (II) is a divalent mononuclear or polynuclear aromatic linking group selected from but not limited to the group consisting of

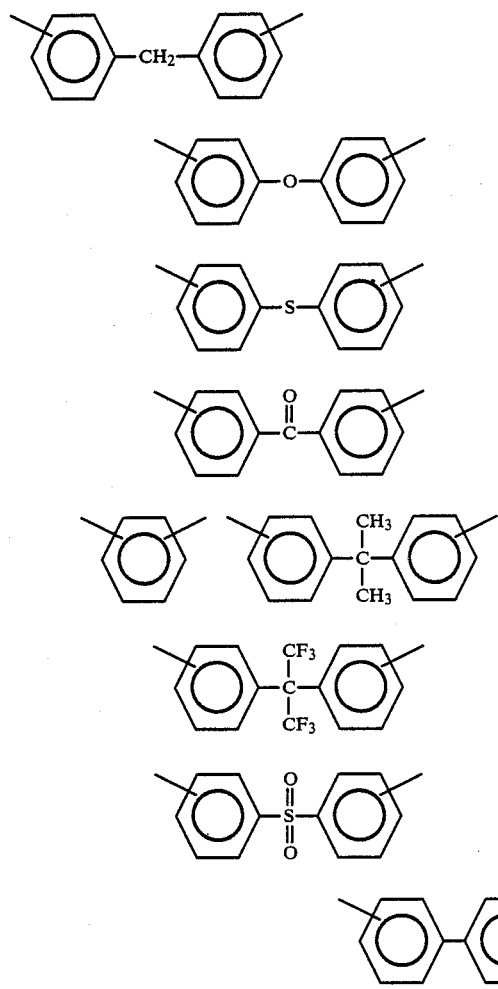

where in the above divalent mononuclear or polynuclear aromatic linking group, one or more of the aromatic nuclei may be substituted by a halogen atom (e.g., fluorine, chlorine, bromine, or iodine), an alkyl group (e.g., having 1 to 4 carbon atoms), an aryl group, or an arylalkyl group.

More specifically in a preferred embodiment, A is a divalent mononuclear or polynuclear aromatic linking group selected from the group consisting of

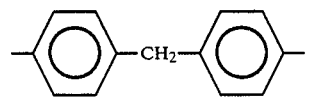

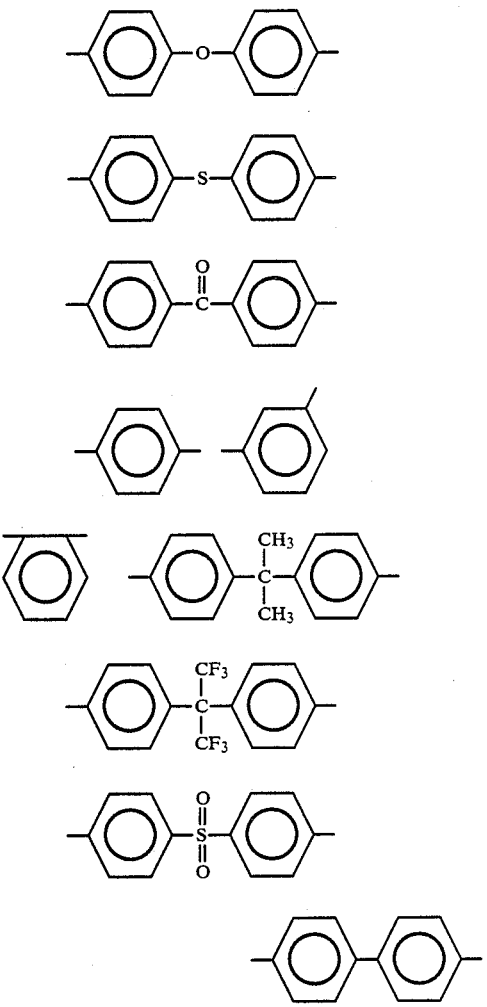

where in the above divalent mononuclear or dinuclear aromatic linking group, one or more of the aromatic nuclei may be substituted by a halogen atom (e.g., fluorine, chlorine, bromine, or iodine), an alkyl group (e.g., having 1 to 4 carbon atoms), an aryl group, or an arylalkyl group.

In accordance with the present invention, aromatic ether bismaleimides of Formula (II) above are produced by the process which comprises first preparing a bismaleamic acid of Formula (III)

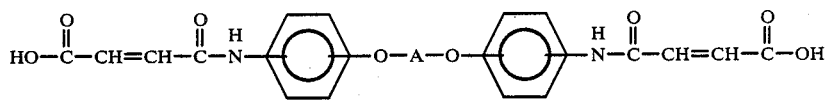

where A is defined as above in Formula (II). This reaction is carried out by adding maleic anhydride to a solution of an aromatic diamine of the Formula (IV)

$$H_2N-\bigcirc-O-A-O-\bigcirc-NH_2$$

wherein A is defined as above in Formula (II) in a solvent under conditions such that the temperature of said maleic anhydride and said diamine does not exceed about 15° C., but preferably such that the temperature does not exceed about 0V C. At a critical point in the reaction, preferably before more than 1.4 mol of maleic anhydride has reacted with 1.0 mol of the aromatic diamine, a trialkylamine is added to the reaction mixture in an amount not in stoichiometric excess of the maleamic acid and in an amount sufficient to materially reduce the viscosity of the reaction medium so that it can be stirred more easily. The trialkylamine reacts to ionize the maleamic acid moeity and form an amine salt. The maleic anhydride addition is continued until the stoichiometrically required amount is added to the reaction mixture. In the second step of the process, an additional quantity of the trialkylamine is added to convert substantially all of the acid groups of the bismaleamic acid to amine salt groups. An imidization catalyst such as nickel (II) acetate and a dehydrating agent such as acetic anhydride are then added and the reaction is continued to convert the maleamic acid groups to imide groups.

By infrared spectra and liquid chromatography data, it has been established that the products prepared by the above process contain at least about 80 weight % of the desired bismaleimide product. Such products have properties which differ significantly from products produced by the prior art processes and are superior in performance properties when employed as resins, and particularly, as impregnating resins in the manufacture of composites and circuit boards.

Other objects and advantages of the invention will be apparent from the following description, the accompanying drawings, and the appended claims.

BRIEF DESCRIPTION OF THE DRAWINGS

FIG. 6 is a liquid chromatographic plot of the product of Formula (I).

DETAILED DESCRIPTION OF THE PREFERRED EMBODIMENT

Figure 1:
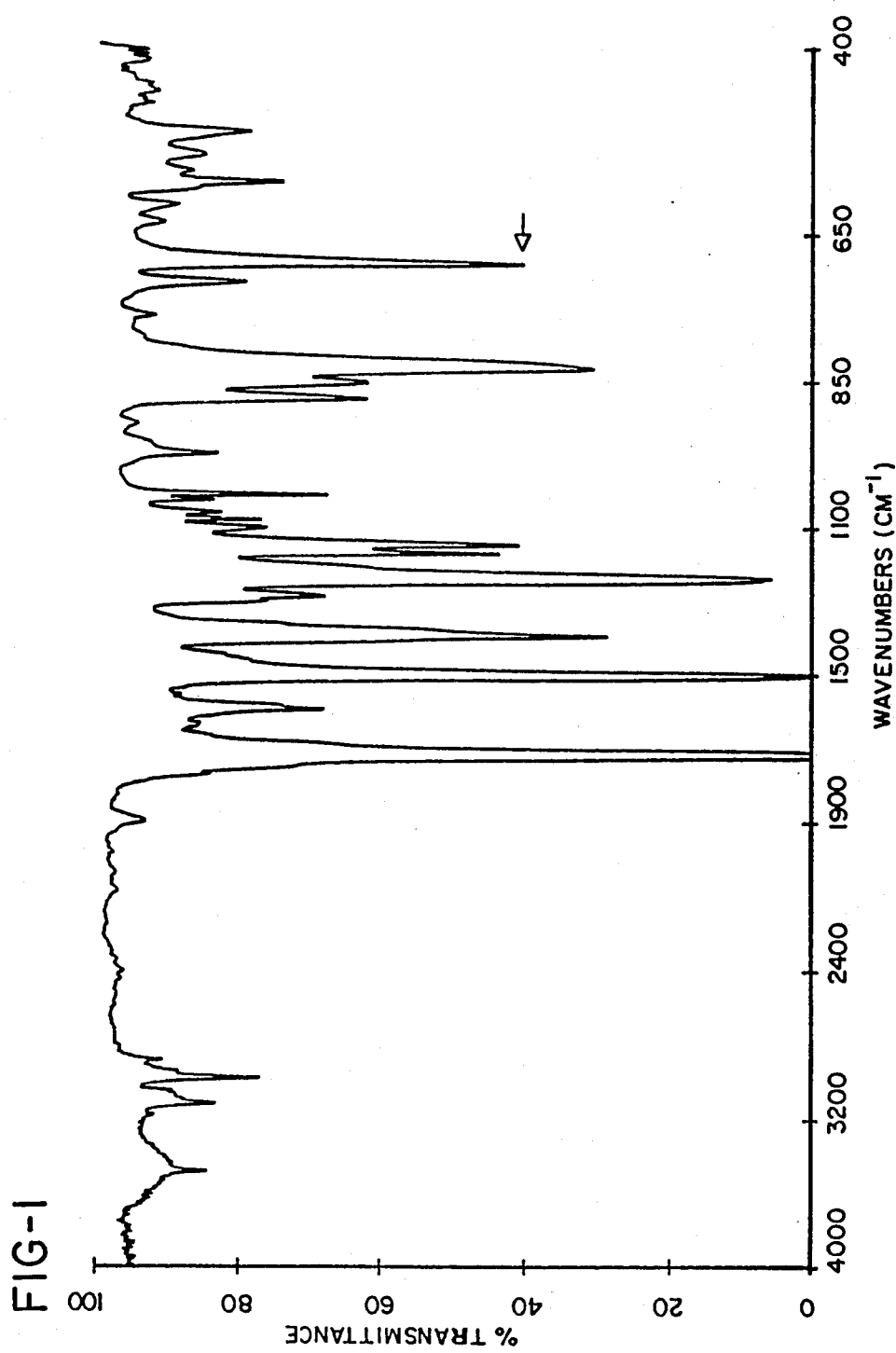
FIG. 1 is aan infrared spectrum of a bismaleimide of Formula (I)

The aromatic diamines employed as starting materials in the manufacture of the bismaleimides of Formulae (I) and (II) may be prepared by following a technique which involves the reaction of the corresponding diphenol with 4-nitrochlorobenzene to produce an intermediate bis-nitro compound. The nitro groups on this compound are subsequently reduced to amine groups in a well-known manner.

In the first step of the process, an aromatic diamine of Formula (IV) is reacted with maleic anhydride to form a maleamic acid intermediate of Formula (III). To provide an efficient economical process, the aromatic diamine is dissolved in a good solvent to prepare a high solids solution containing a minimum concentration of about 0.3 g/ml of solvent, and preferably, about 0.3 to 0.5 g/ml of solvent. Representative examples of solvents useful in the present invention are acetone, dimethylacetamide (DMAC), N-methyl pyrrolidone (NMP), and tetrahydrofuran (THF). These solvents are selected on the basis of the solubility of the diamine therein, their inertness with respect to the starting and intermediate materials, and the ease of removal of the solvent from the final product. Tetrahydrofuran is the preferred solvent because of ease of its removal from the final product. DMAC and NMP can be used but they are more difficult to remove from the final product.

The maleic anhydride is added to the diamine under a combination of conditions of reactant temperature and additoin rate which is designed to maintain the reaction temperature at a temperature below 15° C., preferably at a temperature below 0° C., and more preferably at −5° C. or less. The reaction between the diamine and the maleic anhydride proceeds very quickly. If the temperature becomes too high, the reaction proceeds too quickly and undesirable by-products are formed.

Before reaction, the diamine solution is cooled to 15° C. or less, preferably to a temperature below 0° C., and more preferably to −5° C. or less. The maleic anhydride is preferably added to the diamine as a solution (preferably in the same solvent used to dissolve the aromatic amine) having a concentration of about 0.2 to 0.4 g of maleic anhydride per 1 ml of solvent. This solution can be added to the diamine solution through an addition funnel. The rate of addition of the maleic anhydride solution is adjusted such that the reaction proceeds at a controlled rate. The maleic anhydride solution is typically added slowly to the diamine solution with stirring at the rate of approximately 1 to 3 g/mol aromatic diamine/min., with a preferred rate of 1.50 to 1.70 g/mol aromatic diamine/min.

As the reaction proceeds, the concentration of the maleamic acid product increases and the solubility relationships in the reaction medium change. Eventually, typically when about 1.25 to about 1.40 mol of maleic anhydride has been reacted with 1.0 mol of aromatic diamine, the maleamic acid product precipitates. The reactoin mixture becomes too thick to stir and has the appearance of an aerosol foam.

The discovery has been made that the addition of a trialkylamine to the reaction mixture prevents precipitation of the maleamic acid products and the rapid build-up of viscosity. The trialkylamine ionizes the maleamic acid intermediate to form an amine salt such that the reaction product remains soluble and does not precipitate from the reaction solution. A preferred trialkylamine useful in the present process is triethylamine, but other liquid trialkylamines such as tripropylamine and tributylamine may also be used.

The trialkylamine can be added in periodic increments or in a single charge subject to the consideration that the concentration of unreacted maleic anhydride is minimal (to avoid possible rearrangements of maleic anhydride) and that the trialkylamine is not added in stoichiometric excess of the maleamic acid content. The trialkylamine is added in at least the minimum amount sufficient to materially reduce the viscosity of the reaction medium so that it can be stirred more easily. Since the trialkylamine is employed for another purpose in the second step of the overall process, it is convenient to add the trialkylamine in an approximate stoichiometric quantity. The trialkylamine is usually added to the reaction mixture at a rate of approximately 2 to 8 g/mol aromatic diamine/min. The rate is controlled so that the temperature is maintained within the limits earlier noted, viz. below about 15° C., preferably below 0° C., and more preferably −5° C. or less.

After the trialkylamine addition is completed, the addition of maleic anhydride is continued. The total amount of maleic anhydride added is less than, equal to, or greater than 2 mols maleic anhydride/mol aromatic diamine (i.e., a stoichiometric excess), and typically, about 2.0 to 2.5 mols per mol diamine.

After the addition of the maleic anhydride is completed, the reaction solution is allowed to increase in temperature gradually to insure that all of the diamine has reacted. For example, the reaction solution can be allowed to heat to 20° C. for about 1 hour and then to 60° C. for 30 minutes which forces the reaction to completion so that any unreacted diamine will react to form maleamic acid products.

The prodcuts formed as described above consist predominantly of bismaleamic acids conforming to Formula (III). Where these products are desired for purposes other than conversion to bismaleimides of Formula (II), they can be recovered, isolated, and purified by techniques readily apparent to those skilled in the art.

To convert the bismaleamic acid products prepared above to desired bismaleimides of Formula (II), the following procedures are employed. A further quantity of trialkylamine is added to the previous reaction mixture to convert substantially all of the maleamic acid groups to the corresponding amine salt. The further alkylamine so added serves as a co-catalyst for the ring closure reaction. The reaction mixture is cooled to a temperature of 15° C. or less before the trialkylamine is added, and the addition is made at a rate such that the temperature does not exceed this limit. This temperature reduction is necessary because at higher temperatures, the maleamic acids can isomerize to fumaric acids, undesired by-products.

With formation of the maleamic acid completed, the process moves to the second stage, namely, formation of the maleimide rings. The ring closure reaction is customarily accomplished through use of a ring closure catalyst and a dehydration agent added directly to the maleamic acid product. In this process, the ring closure catalyst and dehydration agent are added to the amine salt of the maleamic acid. In this invention, it has been found that the preferred ring closure catalyst is nickel (II) acetate and the preferred dehydration agent is acetic anhydride. The nickel (II) acetate is used with the trialkylamine salt as a co-catalyst for maximum effectiveness. Nickel acetate, sodium acetate, or excess triethylamine, for example, can be used alone in catalytic amounts, but results in a slower reaction rate and a product with higher concentrations of by-products.

After liquid acetic anhydride and dry nickel (II) acetate tetrahydrate are added to the reaction mixture, the reaction mixture is held at an elevated temperature for 1 to 3 hours but preferably for 1.5 hours. A preferred temperature range is 55 to 65° C. The acetic anydride is added to the reaction mixture in an amount of approximately 222 to 246 ml/mol maleamic acid. The nickel (II) acetate tetrahydrate is added to the reaction mixture in an amount of approximately 11 to 13 g/mol maleamic acid.

Various methods can be used to recover the aromatic ether bismaleimide product. One example of a recovery method is as follows.

The solvent is removed under a vacuum. After the solvent has been removed from the reactoin mixture, the resultant syrup is poured into ice water while stirring very rapidly. The mixture must be stirred with good shear in order to promptly quench the mixture so that the resulting powder is very fine. Otherwise, an agglomeration will result.

The resulting slurry is allowed to stand for 18 hours. The solid is collected by filtration and washed twice with cold water. The solid is air dried for 18 hours.

The process of the invention provides compositions which contain at least 80 weight % of the desired bismaleimide product of either Formula (I) or Formula (II). Such compositions differ significantly from prior art products which reportedly are bismaleimides of Formula (I) or Formula (II), but which in fact contain very large concentrations of by-products resulting from isomerization reactions and an evident failure to obtain significant yields in the dehydration/ring closing reaction of the maleamic moeities to form the desired imide moieties. The factual data supporting the above conclusions are discussed infra.

A composition which contains at least 80 weight % of the bismaleimide of Formula (I) will be characterized in:

(a) being curable to a thermoset resin by the application of heat, (b) having a glass transition ($T_g$) endotherm of about 65° C. and a reaction exotherm peak of about 240° C. as measured by differential scanning calorimetry at a heating rate of 10° C./min., (c) having a viscosity of less than about 300 poises at 120° C., (d) having the following solubilities, in weight %, at 25° in the following solvents:
  (i) Dioxane—ca 16%
  (ii) Methylene Chloride—ca 44%
  (iii) Tetrahydrofuran—ca 39%
  (iv) Toluene—ca 4%
  (v) Acetone—ca 55%

(e) having an infrared spectrum corresponding substantially to FIG. 1 of the drawings, (f) having a strong infrared absorption peak at about 690cm$^{-1}$, (g) having, in a fully cured state, a glass transition temperature of at least about 300° C., (h) having, as a fully cured compressoin molded, neat resin, a moisture uptake of only about 2 weight % when exposed to boiling water for 96 hours, said moisture containing specimens retaining at least about 70% of the dynamic modulus values of the bone dry specimens when measured at temperatures up to 300°, and (i) releasing only about 2 weight % of volatiles when heated to 300° at a heating rate of about 10° C./min.

The concentration of the desired bismaleimide component in a composition can be determined by a number of analytical techniques. The method used in obtaining the data reported herein was a Reverse Phase High Pressure Liquid Chromatography separation. This method is well known in the art. Briefly, in the work reported herein, a sample of the composition is dissolved in dioxane (0.1 weight % solids). This sample is passed through a packed column and the sample is sorbed on the packing. The sorgbed sample is eluted with a dioxane-water mixture of constantly changing proportions. The dioxane-water proportions are controlled and changed by the instrument. The eluting solvent is passed through an ultraviolet light detector which continuously measures solute concentration. The detector output signal is plotted v. time to produce linear plots in which the vertical peaks represent a single component present in the sample. The area under each peak represents the concentration of that eluted component. By comparing the areas under each peak, the concentration of any component in the sample can be expressed quantitatively.

The present invention is more fully illustrated bvy the following non-limiting Examples.

EXAMPLE I

Part A—Preparation of Bismaleamic Acid

To a 5-liter flask equipped with two addition funnels, mechanical stirrer, reflux condenser, thermometer, and $N_2$ inlet tube, were added 500 g (1.218 moles) of 2,2-bis[4-(4-aminophenoxy)phenyl] propane and 1300 ml of tetrahydrofuran. The reaction solution was cooled to −5° C. by means of an external acetone/dry ice bath. To the addition funnel was added a solution of 239 g (2.437 mol) of maleic anhydride dissolved in 810 ml of tetrahydrofuran. This solution was added slowly to the reaction flask with stirring while maintaining the temperature of the reaction at −5° C. When 66.6% of the maleic anhydride solution (approximately 80 minutes) has been added, this addition was stopped. Into the second addition funnel was placed 150 ml (108.9 g; 1.076 mol) of triethylamine and added slowly to the reaction mixture, still maintaining the temperature at −5° C. When the triethylamine addition was completed, the addition of the maleic anhydride solution was continued. The total time for the two maleic anhydride additions was two hours. The reaction mixture was stirred an additional hour at −5° C. The cooling bath was removed and the mixture stirred one hour at 20° C. A heating mantle was added and the reaction mixture was heated to 60° C. for 30 minutes.

Part B—Preparation of Bismaleimide

The reaction mixture of Part A containing the bismaleamic acid intermediate product was cooled to −5° C. At this temperature, 530 ml (384.8 g; 3.802 mol) of triethylamine was slowly added, keeping the temperature at −5° C. Then 285 ml (308.4 g; 3,021 mol) of acetic anhydride and 15 g (0.060 mol) of nickel (II) acetate tetrahydrate were added and the reaction mixture was heated to 60° C. and held at that temperature for 1.5 hours. At this time, the heating mantle was turned off and vacuum applied to the system to remove the tetrahydrofuran. Once the tetrahydrofuran had been removed from the reaction mixture, the resultant syrup approximately 400 ml portions) was poured into 2400 ml of ice water while stirring very rapidly. The slurry which resulted was allowed to stand for 18 hours. The solid was collected by vacuum filtration and washed two times with 2 liters of cold water each time. The solid was air dried for 18 hours. The yield was 690 g(1.209 mol; 99% yield).

EXAMPLE II

Part A—Preparation of Bismaleamic Acid

To a one-liter flask equiped with two addition funnels, mechanical stirrer, reflux condenser, thermometer, and $N_2$ inlet tube, were added 100 g (0.342 mol) of 1,3-bis(4-aminophenoxy)benzene and 300 ml of tetrahydrofuran. The reaction solution was cooled to −5° C. by means of an external acetone/dry ice bath. To one of the addition funnels were added a solution of 67.8 g (0.691 mol) of maleic anhydride dissolved in 160 ml of tetrahydrofuran. This solution was added slowly to the reaction flask with stirring while maintaining the temperature of the reaction at −5° C. When 66.6% of the maleic anhydride solution (approximately 80 minutes) has been added, this addition was stopped. Into the second addition funnel was placed 42 ml (30.5 g; 0.301 mol) of triethylamine and added slowly to the reaction mixture, still maintaining the temperature at −5°. When the triethylamine addition was completed, the addition of the maleic anhydride solution was continued. The total time for the two maleic anhydride additions was two hours. The reaction mixture was stirred an additional hour at −5° C. The cooling bath was removed and the mixture stirred one hour at 20° C. A heating mantle was added adn the reaction mixture was heated to 60° C. for 30 minutes.

Part B—Preparation of Bismaleimide

The reaction mixture of Part A containing the bismaleamic acid intermediate product was cooled at −5° C. At this temperature, 147.5 ml (107.1g; 1.058 mol) of triethylamine was slowly added, keeping the temperature at −5° C. Then 80 ml (86.6 grams; 0.848 mol) of acetic anhydride and 2 g (0.008 mol) of nickel (II) acetate tetrahydrate were added and the reaction mixture was heated to 60° C. and held for 1.5 hours. At this timme, the heating mantle was turned off and vacuum applied to the system to remmove tetrahydrofuran. Once the tetrahydrofuran had been removed from the reaction mixture, the resultant partially crystalline syrup was poured into 2500 ml of ice water while stirring very rapidly. The solid was collected by vacuum filtration and washed two times with 500 ml of cold water each time. The solid was air dried overnight. A yield of 155 g (0.342 mol; 100% yield) was obtained.

EXAMPLE III

Using the same reaction procedures of Examples I and II and the proper molar ratio of reactants, a bismaleimide was prepared from 2,2-bis[4-(4-aminophenoxy)phenyl]hexafluoropropane. Starting with 100 g (0.193 mol) of the diamine, 130 g (0.192 mol; 99% yield) of the bismaleimide was obtained.

EXAMPLE IV

Another bismaleimide product was prepared in essentially quantitative yield following the general employed was prepared by first reacting 4-nitrochlorobenzene with a commerical mixed isomer sample of bishydroxyphenyl methanes and subsequently reducing the intro groups to amine groups.

The properties of a bismaleimide of Formula (I)—sometimes identified as 2,2-bis[4-(4-maleimidophenoxy)phenyl]propane or BPA-BMI for convenience of expression - prepared in general in accordance with the process of Example I was evaluated for certain performance properties as a thermosetting resin. The results of this evaluation were reported at the Spring 1986, Conference of the Society of Plastics Engineers. This paper was published in Volume 32 (1986), pages 1311–1315 of the Society of Plastics Engineers Technical Papers. The entire disclosure of this paper is incorporated herein by reference. Relevant portions of this paper are reproduced below.

NEAT RESIN CHARACTERIZATION

A differential scanning calorimetry scan (FIG. 1)* of 2,2-bis[4-(4-maleimidophenoxy) maleimidophenoxy)phenyl) propane, BPA-BMI, showed a $T_g$ for the uncured resin around 70° C. with a maximum peak exotherm in the vicinity of 210° C. The heat of reaction was on the order of 30 cal/g. The observation that the uncured material had a $T_g$ around 70° C. gave the BPA-BMI the potential for being hot melt prepreggable. An iso-conversion kinetic plot (FIG. 2)* based on the rate equation $d\alpha/dt = k(1-\alpha)^n$ was obtained for the BPA-BMI. Using a degree of conversion of 25% to reach the gel point, the plot indicated that gelation occurred in 60 minutes at 180° C. This observation was consistent with other gel time determinations. Using the glass cloth impregnated sample and a typical cure cycle for commerically available BMIs (2 hour cure at 200° C., followed by a 5 hour post-cure at 250° C.), the resultant BPA-BMI was analyzed by dynamic mechanical analysis (DMA). The initial DMA scan (FIG. 3)* showed a $T_g$ of 240° C. (464° F.). However, additional curing was observed to occur in the material while being heated to 350° C. under a nitrogen atmosphere within the DMA heating compartment. A DMA rescan (FIG. 4)* of the same sample indicated at the $T_g$ was now in the vicinity fo 360° C. (680° F.).
*This Figure is not reproduced.

Cast samples of the BPA-BMI cured by compression molding techniques showed similar results. That is, the first DMA scan indicated a relatively low Tg material, while the DMA rescan for the same sample (after being heated through the first scan) showed a higher value of Tg. It is clear that after the initial two hour cure of 200° C. and five hour post-cure at 250° C., the BPA-BMI has not fully cured because the Tg advances during the DMA scan. THe fully cured $T_g$ of the BPA-BMI is in the vicinity of 360° C. (680° F.). The density of the cast specimen was 1.26 g/cc. and its moisture retention was 1.6% maximum when exposed to 100% R.H.

Figure 5:
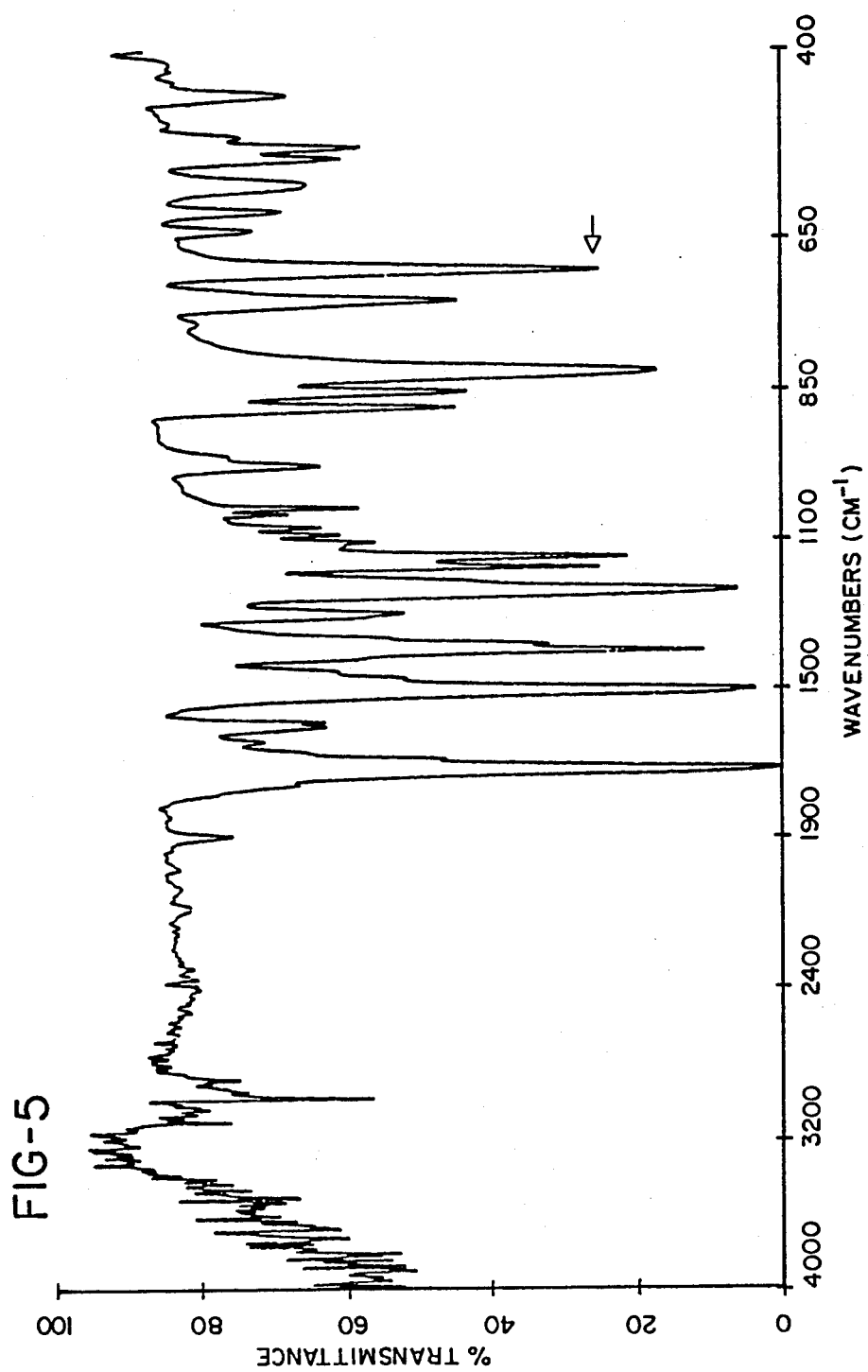
FIG. 5 is an infrared spectrum of a product offered for experimental use by a U.S. manufacturer and which is reported to be the bismaleimide of Formula (I)

A cast specimen of the BPA-BMI has been exposed to boiling water for 96 hours and tested by DMA. The total moisture uptake of this specimen was 2.1%. The DMA data (FIG. 5)* compared modulus and loss tangent values for the wet sample to a comparable dry specimen. The data show relatively little influence of moisture on the properties. This observation is even more evident at high temperatures as illustrated in Table I.
*This Figure is not reproduced.

Neat resin dogbone microtensile specimens were compression molded from the BPA-BMI. The specimens were cured using the following cycle: 180° C. hold for 14 min; apply 600 PSI pressure and an additional 46 min hold at 180° C.; heat to 200° C. and hold for one hour. After the cure cycle, the specimens underwent a free-standing post-cure at 250° C. for five hours. The mechanical testing results indicated a neat resin potential for tensile modulus in the range of 500 ksi ($3.4 \times 10^9$ pa) and ultimate tensile strength of the order of 7 ksi ($4.8 \times 10^7$ pa) with elongation values of approximately 1.5%. A second set of microtensile specimens post-cured at 250° C. for 16 hours gave similar results.

It should also be pointed out that the microtensile specimens prepared were not brittle in comparison to similar samples of commercially available BMIs.

PREPREG FABRICATION

As mentioned earlier, since the uncured BPA-BMI showed a Tg in the vicinity of 70° C., it was believed that this material was amenable to hot melt prepregging. Initial studies indicate that the BPA-BMI can indeed be hot melt prepregged. The material heated above its uncured glass transition temperature and applied to fiber reinforcement flows and wets fibers readily.

The disadvantage of this material in a hot melt prepregging application occurs once the resin cools down below its uncured $T_g$. The resultant prepreg is boardy and lacks tack and drape. Experiments are underway to improve on this fabrication drawback. The BPA-BMI is being formulated with additives known to improve on the tack and drape of commercially available BMIs. Initial results indicate that the BPA-BMI can be formulated to a lesser extent than known commercial BMI formualations. Thus, the overall thermal stability and mechanical properties of the BPA-BMI formulations are affected less in comparison to BMI formulations which contain high levels of non-BMI type additives.

Solution prepregging of the BPA-BMI appears to cause no significant problems. The material is very soluble in a host of common organic solvents. Acceptable tack and drape can be maintained with residual solvent.

CONCLUSIONS

The series of aromatic ether bismaleimides discussed in this work meets the new requirements needed for matrix resins.

The ones studies to date, in particular the BPA-BMI, have high thermal stability. In fact, the Tg of the fully cured BPA-BMI surpasses the Tg's of some of the polyimides which are used in very high temperature applications [288° C. (550° F.)]. These flexible-type aromatic ether BMIs exhibit low moisture sensitivity, and the BPA-BMI has been fabricated into non-brittle specimens.

TABLE 1

| COMPARISON BETWEEN WET AND DRY MODULUS VALUES FOR BPA-BMI AT SELECTED TEMPERATURES | | | | |
|---|---|---|---|---|
| Temperature | | Modulus, GPa | | % Modulus |
| °C. | (°F.) | dry | wet | Retention |
| 240 | (464) | 0.981 | 0.837 | 85 |
| 280 | (536) | 0.895 | 0.720 | 80 |
| 320 | (608) | 0.830 | 0.597 | 72 |

The neat resin mechanical properties of this resin were:
Modulus: 500 ksi
Ultimate strength: 8 ksi
Elongation: 1.5–2%
Compares favorably to others e.g., for neat resin MDA-BMI
Elongation: 1.0% or less
The neat resin dielectric properties of this resin were:

| FREQUENCY | DIELECTRIC CONSTANT | DISSIPATION FACTOR |
|---|---|---|
| 1 kh$_z$ | 3.24 | — |

| FREQUENCY | DIELECTRIC CONSTANT | DISSIPATION FACTOR |
|---|---|---|
| 8 kh$_z$ | 3.23 | 0.0012 |
| 128 kh$_z$ | 3.21 | 0.0058 |
| 1 mh$_z$ | 3.18 | 0.0089 |
| 4 mh$_z$ | 3.19 | 0.0151 |

The resin was analyzed by the Reverse Phase High Pressure Chromatographic method discussed supra to establish the purity of the resin. The chromatogram plot is shown as FIG. 6 of the drawings. The sample contained well in excess of 80 weight % of the BPA-BMI component.

FIG. 1 of the drawings is an infrared spectrum of a BPA-BMI product corresponding to Formula (I) and which was prepared by a procedure corresponding to Example I. It will be noted that the spectrum has a strong absorption peak at about 690cm$^{-1}$. This peak is indicated by the arrow in the drawing.

The solubility of a product prepared by a procedure corresponding to Example I in several solvents was measured. The solubilities in weight % at 25° C. were:

| Solvent | Wt. % Dissolved at 25° C. |
|---|---|
| Dioxane | Ca 16% |
| Methylene Chloride | Ca 44% |
| Tetrahydrofuran | Ca 39% |
| Toluene | Ca 4% |
| Acetone | Ca 55% |

Example I of U.S. Pat. No. 4,460,783 reports that the BPA-BMI product of Formula (I) was prepared by reacting maleic anhydride with 2,2-bis[4-(4-aminophenoxy)phenyl]propane in acetone to prepare an intermediate bismaleamic acid product which then was reacted with acetic anhydride in the presence of potassium acetate at a temperature of 80°-100° C. The patentees reported that the product ostensibly having structure of Formula (I) was recovered from the acetone reaction medium by filtration. In effect, the patentees have indicated that his product has a very low solubility in acetone.

Since the product produced by the applicants' method and reportedly having the structure of Formula (I) is highly soluble in acetone whereas the reportedly indentical product produced in Example I of U.S. Pat. No. 4,460,783 is insoluble in acetone, it necessarily follows that the two products do not have the same compositions. The applicants therefore have carried out certain experiments to establish the difference existing between products of supposedly identical composition.

COMPARATIVE EXAMPLE I

In considering the experimental conditions used to duplicate the work of Example I of U.S. Pat. No. 4,460,783, it was noted that an ambiguity was present or one or more reaction parameters were not set forth. Specifically, at column 7, lines 5 and 6, it is stated that the reaction, in an acetone solvent, was carried out at 80°-100° C. Since acetone has an atmospheric bp of 56° C., this statement cannot be correct, unless the reaction was carried out in a pressurized reactor. It is most likely that the patentee intended to state that the reaction vessel was heated to 80°-100° C., possibly in an oil bath, with the reaction mixture attaining the temperature of the refluxing solvent, i.e., the acetone. Based on this assumption, the following work was carried out.

An apparatus was assembled and consisted of a 500 ml, 3-necked, round bottom flask equipped with a condenser, an overhead stirrer, an addition funnel, and an inlet for nitrogen gas. An initial charge of 200 grams of reagent grade acetone and 20 grams (0.05 mol) of 2,2-bis[4(40aminophenoxy)phenyl]propane was made to the apparatus. The mixture was cooled using a dry ice/acetone bath to 0°-5° C. Then, 10.0 grams (0.10 mol) of freshly ground maleic anhydride was added to the reaction mixture. The mixture was stirred for three hours. The initial mixture was a light brown, clear solution. Ten minutes of mixing at 0°-5° C. produced a cloudy yellow mixture. The flask and its contents were removed from the dry ice/acetone bath after three hours. Ten (10.0) grams of acetic anhydride and 0.05 gram of potassium acetate were added to the mixture. No apparent physical changes occurred. The reaction mixture was heated to 60° C. over a period of about 45 minutes and maintained at this temperature for 30 minutes. The flask was then transferred to a 90° C. oil bath. After 50 minutes, the reaction flask and its contents were removed from the oil bath. No apparent loss of acetate occurred. The reaction mixture maintained the cloudy yellow color throughout the reaction up to completion of the experiment.

After cooling, the solid was filtered off and the reaction flask was rinsed out with reagent grade acetone to remove all of the solid. The solid was then washed with water and air dried overnight. The weight of the solid was 26.5 grams. The solid was insoluble in water and dioxane.

Figure 3:
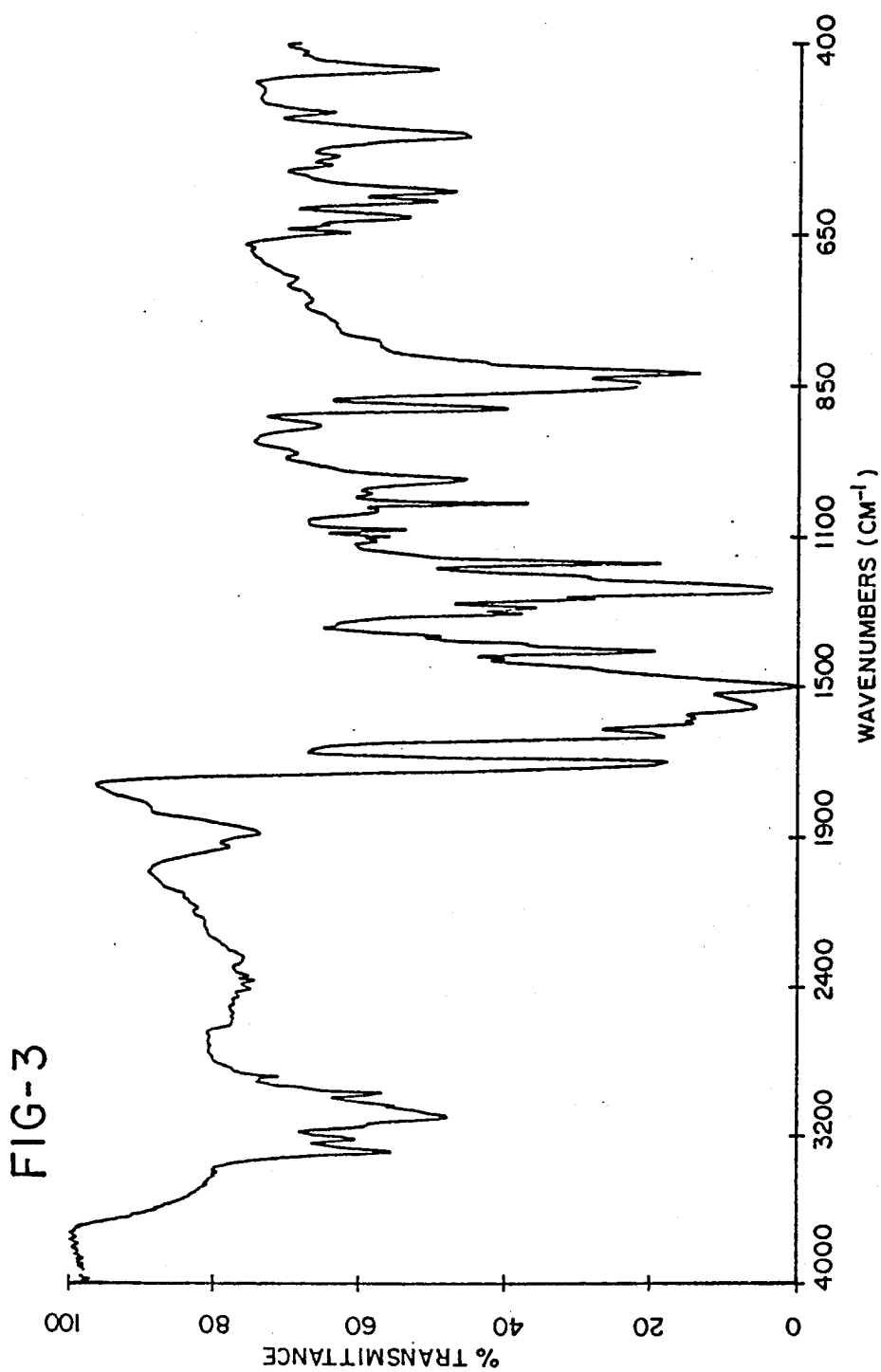
FIG. 3 is an infrared spectrum of a product prepared by a process corresponding to Example 1 of U.S. Pat. No. 4,460,763.

FIG. 3 is an infrared spectrum of a product prepared by the foregoing procedure. The spectrum has no absorption peak at 690cm$^{-1}$ as shown in the infrared spectrum of FIG. 1. Accordingly, the product is not the bismaleimide product of Formula (I).

The product was characterized in a Differential Scanning Calorimeter (DSC) run at a heating rate of 10° C./min. An endotherm occurred at 160° C. Thermogravimetric analysis (TGA) indicated a release of about 14 weight % volatiles when heated to 300° C. and decomposition at 375° C. The product could not be analyzed by the Reverse Phase High Pressure Chromatographic method discussed supra as the product was insoluble in dioxane. Because of its high volatiles, the product has poor resin processability. The product was found to be insoluble in dioxane, methylene chloride, THF, toluene, and acetone.

A small quantity of a by-product was recovered from the filtrate of this run. The by-product, after drying, weighed less than 5.0 grams and had a gooey consistency. In view of the sample size and consistency, no evaluation was made of it.

COMPARATIVE EXAMPLE II

An attempt was made to prepare a bismaleimide of Formula (I) by following general procedures shown in U.S. Pat. No. 3,839,287.

The apparatus employed consisted of a 2 liter, 3-necked, round bottom flask equipped with an overhead mechanical stirrer, an inlet for nitrogen gas, and a thermometer. An initial charge of 82.1 grams (0.2 mol) of 2,2-bis[4-(4-aminophenoxy)phenyl]propane and 400 ml of N,N-dimethylacetamide was made to the apparatus. After all the solid dissolved, the reaction mixture was cooled to 0° C. A charge of 39.22 grams (0.4 mol) of dry maleic anhydride was made in increments at a rate such that the solution temperature did not exceed 10° C. The reaction mixture was then allowed to stir at 10° C. for another hour. A charge of 40.8 grams (0.4 mol) of acetic anhydride and 4 grams (0.04 mol) of triethylamine was made to the reactor and the reaction mixture was stirred for 4 hours at ambient temperature. The reaction mixture was added dropwise with efficient stirring to a large volume of water. A yellow solid kicked out of solution. The solid was separated by filtration and washed repeatedly on a filter until the washings had the pH of tap water. The dry solids weighed 91.7 grams for a 80.4% yield.

Figure 4:
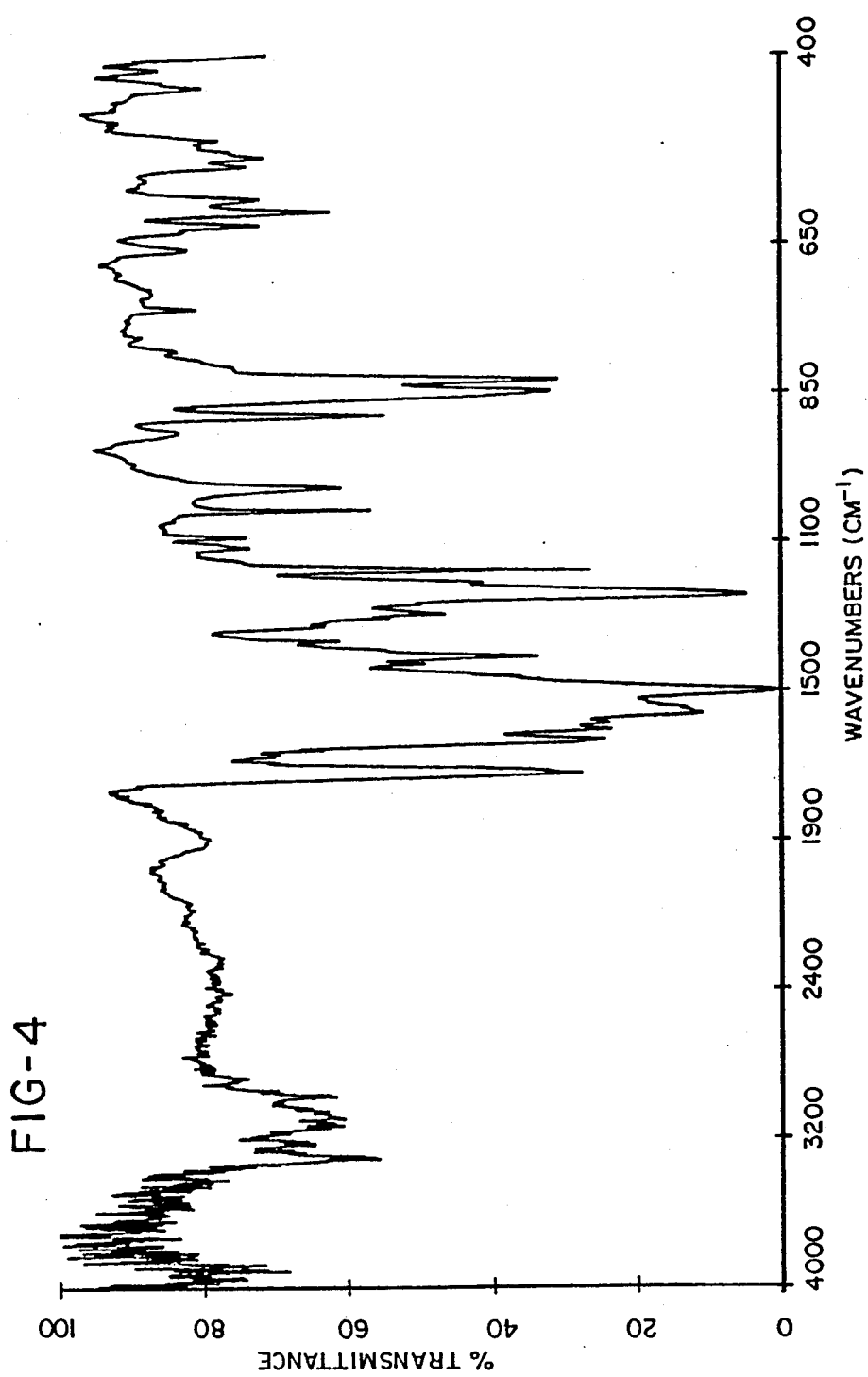
FIG. 4 is an infrared spectrum of a product prepared by a process corresponding to U.S. Pat. No. 3,839,287.

FIG. 4 is an infrared spectrum of a product prepared by the foregoing procedure. The spectrum does not contain a strong absorption peak at 690cm$^{-1}$ as did not infrared spectrum of FIG. 1.

The product was characterized in a Differential Scanning Calorimeter (DSC) run at 10° C./min. A Tg endotherm occurred at 60° C. and an endotherm occured at 193° C. followed by an exotherm at about 210° C. A thermogravimetric analysis (TGA) showed a release of 12.5 weight % volatiles when heated to 30° C. and decomposition at 400° C. The resin could not be analyzed by the Reverse Phase High Pressure Chromatrographic method discussed supra as the product was insoluble in dioxane. Because of its high volatiles, the product has poor resin processability. The product was found to be insoluble in dioxane, methylene chloride, THF, toluene, and acetone.

COMPARATIVE EXAMPLE III

Figure 2:
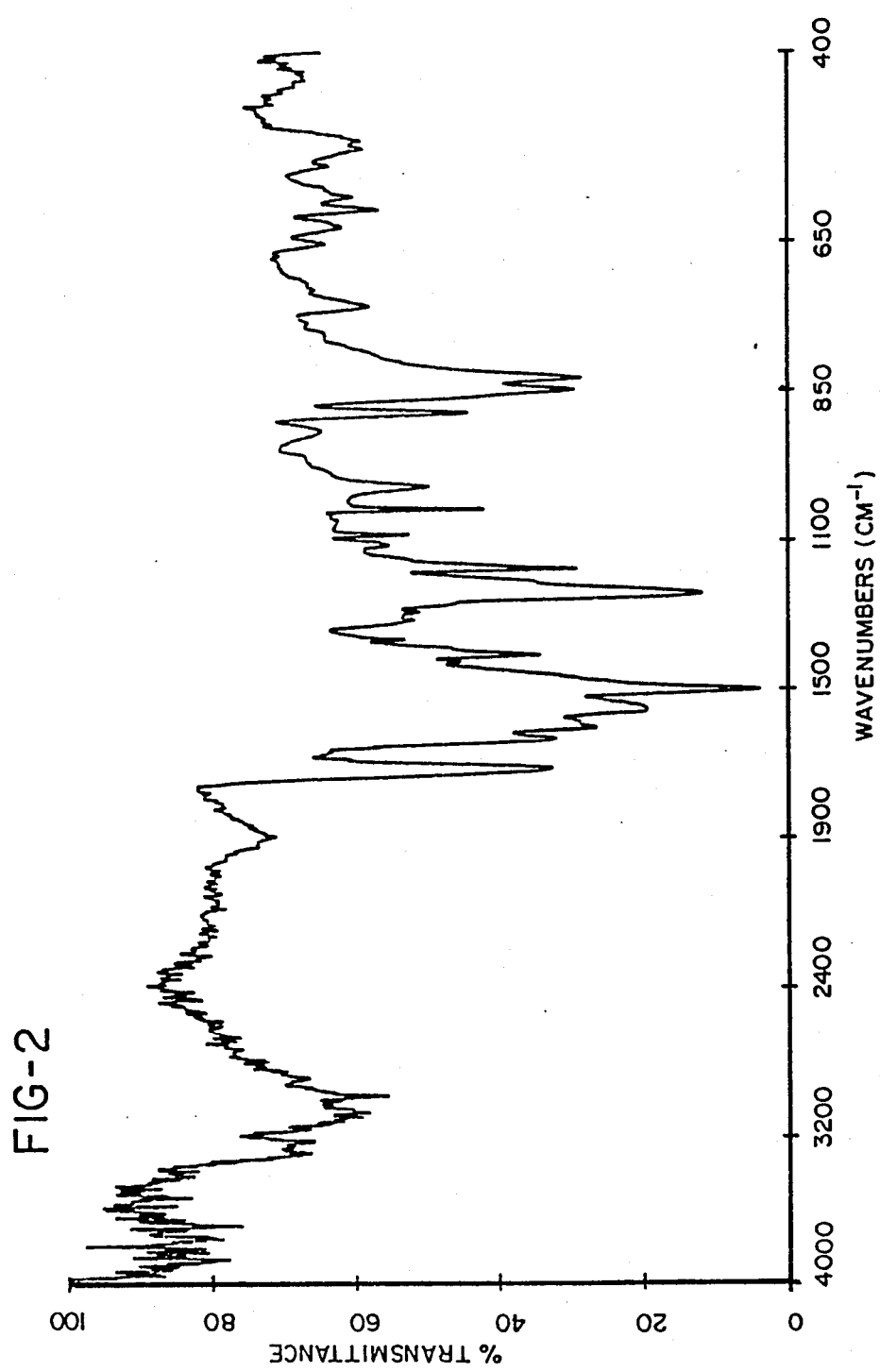
FIG. 2 is the infrared spectrum of the bismaleamic acid precursor of the bismaleimide of Formula (I)

To provide a control, an authentic sample of the bismaleamic acid of Formula (III) was prepared. A charge of 102.8 grams (0.25 mol) of 2,2-bis[4-(4-aminophenoxy)phenyl]propane was dissolved in 1400 ml of THF. The solution was cooled to about −11° C. in a dry ice/acetone bath. A solution of 49.6 grams (0.50) of high purity maleic anhydride in 225 ml of THF was added to the stirred diamine solution over 20 minutes. After this addition was completed, a yellow precipitate began forming. Stirring was continued at −10° C. for 1 hour, then raised to 25° C. and maintained at 25° C. for 1 hour, and then slowly increased to 65° C. The reaction mixture continued to thicken throughout this heating cycle. The reaction mixture was cooled to 20° C., filtered, pressed free of solvent, and air dried overnight. The recovered solids weighed 132 grams (76% of theory). An infrared spectrum of the product is shown in FIG. 2.

When subjected to analysis in a Differential Scanning Calorimeter with the temperautre increase being 10° C./min., the product showed two endotherms at 135° and 175° C. and an exotherm at about 200° C. Thermogravimetric analysis (TGA) showed a loss of 13.5 weight % when heated to 300° C. followed by decomposition at 400° C. The product was insoluble in dioxane, methylene chloride, THF, toluene, and acetone. By reason of its insolubility in dioxane, the product could not be analyzed by the Reverse Phase High Pressure Liquid Chormatographic Method discussed supra. By reason of its volatiles loss on heating, the product has poor resin processing characteristics.

COMPARATIVE EXAMPLE IV

A major U.S. Chemical company has recently offered a bismaleimide product reported to have the structure of Formula (I) for evaluation. In view of several prior art workers misidentifying the product of Formula (I), a study of the newly offered product was made to confirm its structure. As infrared spectrum of the product is set forth as FIG. 5. The presence of a band at 690cm$^{-1}$ (shown by the arrow)confirms that the product does indeed contain a fraction having the structure of Formula (I).

The solubility of the product is representative solvents was measured at 25° C. The data are set forth in the Table below:

| Solvent | Weight % Dissolved at 25° C. |
| --- | --- |
| Dioxane | Ca 1% |
| Methylene Chloride | Ca 26.8% |
| THF | Ca 15.5% |
| Toluene | Ca 9% |
| Acetone | Ca 29.2% |

An attempt was made to estimate the product's content of the desired bismaleimide of Formula (I) by the Reverse Phase High Pressure Liquid Chromatographic procedure discussed supra. A valid analysis could not be made as only about 1% of the sample dissolved in dioxane. A chromatographic tracing of the soluble fraction was similar to the curve shown in FIG. 6.

The product had an endotherm at 107° C. when analyzed in a Differential Scanning Calorimeter (DSC) using a heating rate of 10° C./min. In a thermogravimetric analysis (TGA), a volatiles loss of 12.4% was suffered when the sample was heated to 300° C. The sample decomposed at 450° C. By reason of its high volatiles content, the product has no viability as a commercial thermosetting resin.

Having described the invention in detail and by reference to preferred embodiments thereof, it will be apparent that modifications and variations are possible without departing from the scope of the invention defined in the appended claims.

What is claimed is:

1. A process for preparing aromatic ether bismaleimides of the Formula (II)

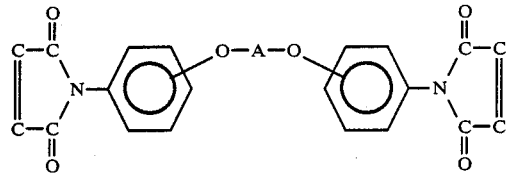

wherein A is a divalent mononcuclear or polynuclear aromatic linking group which comprises:
   (a) adding maleic anhydride to a solution of an aromatic diamine of the Formula (IV)

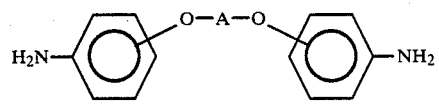

wherein A is defined as in Formula (II) in a solvent such that the temperature of said maleic anhydride and said diamine does not exceed about 15° C. to form a maleamic acid, said maleic anhydride being added in an amount of approximately 1.25 to 1.40 mol of said maleic anhydride per mol of said aromatic diamine;

(b) gradually adding a trialkylamine to said reaction mixture at such a rate to maintain a fluid reaction mixture while also maintaining the temperature of said reaction mixture at less than about 0° C., said trialkylamine ionizing said maleamic acid to form an amine salt and being added in an amount sufficient to maintain said maleamic acid in solution;

(c) subsequently adding sufficient maleic anhydride to said reaction mixture such that the total amount of maleic anhydride added is approximately 2 mols of said maleic anhydride per mol of said aromatic diamine;

(d) adding further alkylamine to said reaction mixture in an amount sufficient to convert the maleamic acid essentially completely to said amine salt and thereby maintain said maleamic acid in solution;

(e) adding an imidization catalyst and a dehydration agent to said reaction mixture; and (f) recovering an aromatic ether bismaleimide of the Formula (II).

2. The process of claim 1 wherein A is a mononuclear or polynuclear linking group selected from the group consisting of

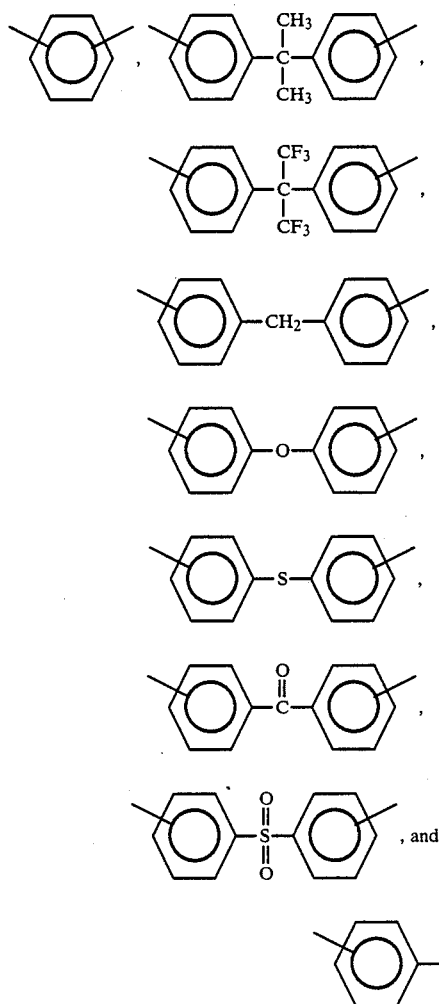

, and wherein said linking group, one or more of the aromatic nuclei may be substituted by a halogen atom, an alkyl group, an aryl group, and an arylalkyl group.

3. The process of claim 2 wherein A is a mononuclear or polynuclear linking group selected from the group consisting of

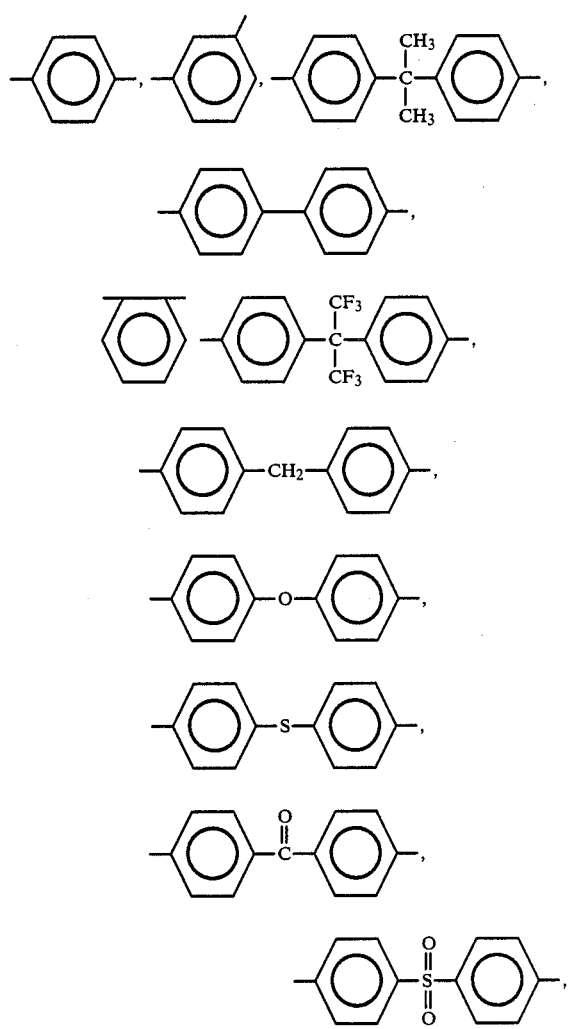

where in said linking group, one or more of the aromatic nuclei may be substituted by a halogen atom, an alkyl group, an aryl group, and an arylalkyl group.

4. The process of claim 3 wherein said aromatic diamine is 2,2-bis[4-(4-aminophenoxy)phenyl]propane.

5. The process of claim 3 wherein said aromatic diamine is 1,3-bis(4-aminophenoxy) benzene.

6. The process of claim 3 wherein said aromatic diamine is 2,2-bis[4-(4-aminophenoxy)phenyl]hexafluoropropane.

7. The process of claim 1 where in step (b), said trialkylamine is triethylamine.

8. The process of claim 7 wherein after subsequently adding said maleic anhydride in step (c), said reaction mixture is maintained at an elevated temperature for a sufficient period of time to permit said diamine to substantially completely react with said maleic anhydride.

9. The process of claim 8 wherein prior to adding said imidization catalyst and said dehydration agent in step (e), said reaction mixture is cooled to a temperature less than about 15° C.

10. The process of claim 9 wherein said step of adding said imidization catalyst and said dehydration agent in step (e) comprises adding acetic anhydride and nickel (II) acetate tetrahydrate to said reaction mixture and heating said reaction mixture.

11. The process of claim 1 wherein the rate of said maleic anhydride addition in step (a) to said reaction mixture is approximately 1 to 3 g/mol aromatic diamine/min.

12. The process of claim 1 where in step (b), the total amount of said trialkylamine added to said reaction mixture is in an amount of about 80 to 100 g/mol aromatic diamine.

13. The process of claim 10 where in step (d), the total amount of said triethylamine added to said reaction mixture is in an amount of about 300 to 330 g/mol aromatic diamine.

14. The process of claim 1 wherein said product aromatic ether bismaleimide of the Formula (II) emits less than 3% volatiles up to 200° C.

15. The process of claim 1 wherein said product aromatic ether bismaleimide possesses a melt viscosity less than about 300 poise at 120° C.

16. The process of claim 1 wherein said product aromatic ether bismaleimide is not substantially thermally polymerizable at temperatures less than about 145° C.

17. The process of claim 1 wherein said solvent is tetrahydrofuran.

18. The process of claim 1 where in step (f), said step of recovering said bismaleimide comprises:
  applying a vacuum to the system to remove said solvent;
  pouring the resulting mixture into ice water while stirring very rapidly;
  collecting the solid by filtration;
  washing the solid with water; and
  air drying the solid.

19. The process of claim 1 where in step (a), the concentration of said aromatic diamine in said solvent is about 0.3 to 0.5 g/ml solvent.

20. In a process for preparing bismaleimidies of Formula (II)

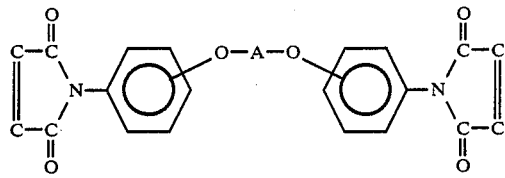

which comprises:
  (a) preparing a solution of bismaleamic acid by adding maleic anhydride to a solution of an aromatic diamine of Formula (IV)

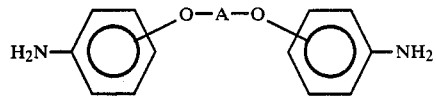

wherein A is defined as in claim 1, (II) in a ratio of 2 mols of maleic anhydride per mol of aromatic diamine while maintaining said reaction mixture at a temperature not exceeding about 15° C. to form aid bismaleamic acid; the improvements which comprise:
  (1) including said aromatic diamine in its solvent in a minimum amount of about 0.3 gram/ml of solvent, and
  (2) adding to said reaction mixture a trialkylamine to ionize said maleamic acid and form an amine salt, said trialkylamine being added in an amount not in stoichiometric excess of said maleamic acid and in an amount sufficient to materially reduce the viscosity of the reaction medium so that it can be stirred more easily.
  (b) adding the quantity of trialkylamine required (if any) to convert substantially all of the acid groups of said bismaleamic acid to amine salts groups,
  (c) adding an imidization catalyst and a dehydration agent to said reaction mixture, and
  (d) recovering a bismaleimide of the Formula (II).

* * * * *

UNITED STATES PATENT AND TRADEMARK OFFICE
CERTIFICATE OF CORRECTION

PATENT NO. : 4,855,450

DATED : August 8, 1989

INVENTOR(S) : John M. Butler, Richard P. Chartoff, James A. Harvey

It is certified that error appears in the above-identified patent and that said Letters Patent is hereby corrected as shown below:

Claim 1, line 51, "mononculear" should be --mononuclear--.

Signed and Sealed this

Third Day of April, 1990

Attest:

HARRY F. MANBECK, JR.

*Attesting Officer*  *Commissioner of Patents and Trademarks*